United States Patent [19]

Tucker

[11] 4,028,534
[45] June 7, 1977

[54] AUTOMATIC SPAN CIRCUIT

[75] Inventor: Huel C. Tucker, Centerville, Ohio

[73] Assignee: The United States of America as represented by the Secretary of the Army, Washington, D.C.

[22] Filed: Apr. 14, 1976

[21] Appl. No.: 676,951

[52] U.S. Cl. .................. 235/151.35; 235/150.5; 307/264; 330/145; 340/347 AD
[51] Int. Cl.² .................. G06F 15/20; G06J 1/02
[58] Field of Search ....... 235/151.3, 151.35, 150.5, 235/150.52, 150.53; 340/347 AD, 347 DA, 15.5 GC; 307/264, 229; 330/127, 129, 145

[56] References Cited
UNITED STATES PATENTS

| | | | |
|---|---|---|---|
| 2,592,308 | 4/1952 | Meacham | 340/347 AD |
| 3,409,251 | 11/1968 | Lawson et al. | 235/150.5 |
| 3,462,588 | 8/1969 | Hussey | 235/150.53 |
| 3,969,683 | 7/1976 | Fabricius | 330/129 |

Primary Examiner—Charles E. Atkinson
Assistant Examiner—Errol A. Krass
Attorney, Agent, or Firm—Nathan Edelberg; A. Victor Erkkila; Thomas R. Webb

[57] ABSTRACT

An analyzer, for measuring the concentration of a particular material in a sample, has its analog voltage output connected to the analog input of a multiplying digital-to-analog converter (MDAC) whose output is connected to a voltmeter and to one input of a voltage comparator having its other input connected to a potentiometer and battery producing a reference voltage somewhat less than the known output voltage of the sample. The comparator output is connected to two gates which control the transmission of electrical pulses from a generator to the UP or DOWN inputs of a binary UP/DOWN counter, having N digital output channels connected to N digital input channels of the MDAC, in such manner that the counter counts UP, increasing the gain of the MDAC, when the MDAC output voltage is lower than the reference voltage, or counts DOWN, decreasing the MDAC gain, when the MDAC output voltage is higher than the reference voltage. After a short time, the gates are closed, to inactivate the comparator and counter, and the circuit is used, with fixed MDAC gain and fixed reference voltage, to measure the output voltage or concentration of an unknown sample. At any time, the circuit can be re-calibrated in the same manner, with a standard sample.

9 Claims, 1 Drawing Figure

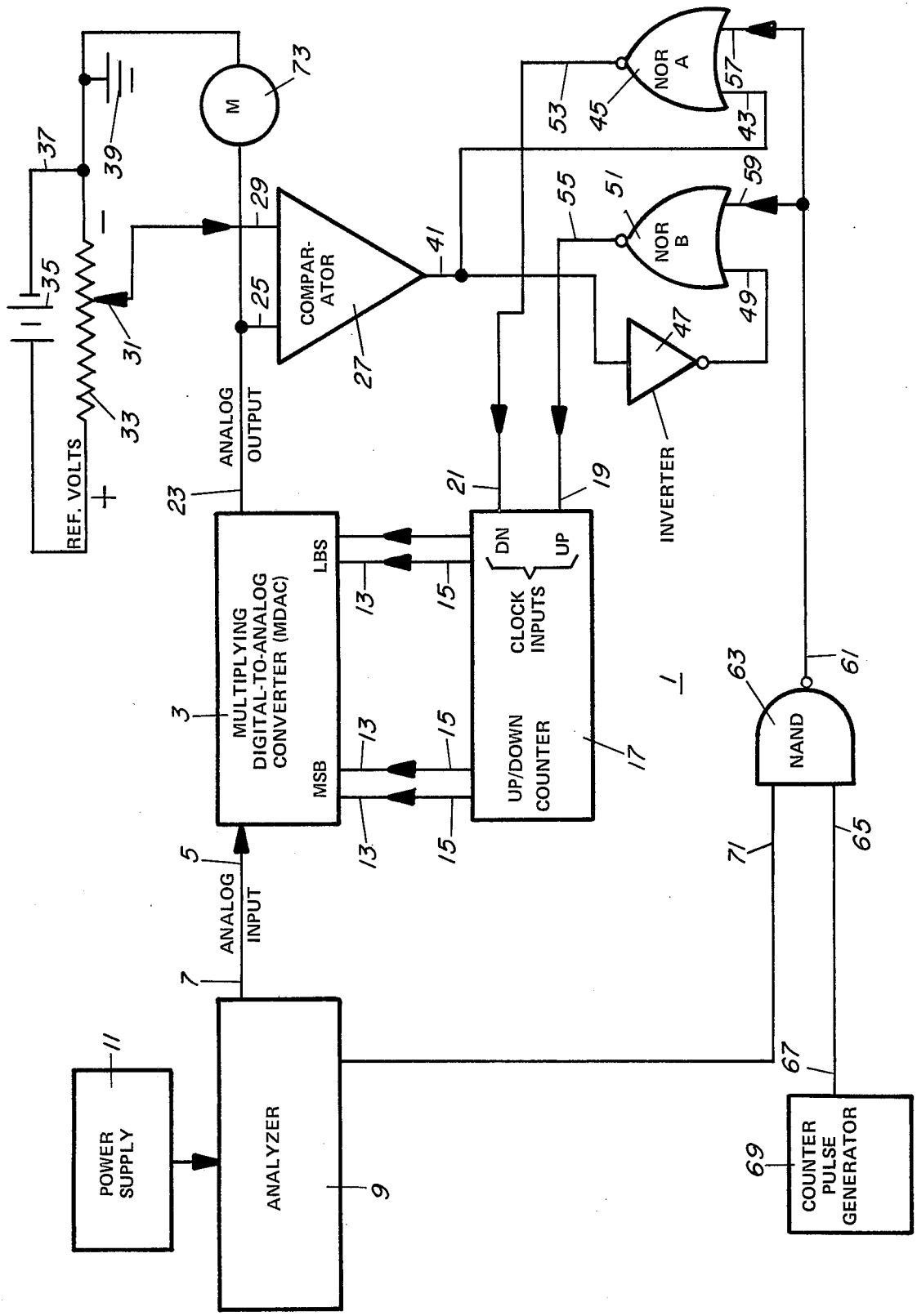

AUTOMATIC SPAN CIRCUIT

GOVERNMENT INTEREST

The invention described herein was made under a contract with the U.S. Government.

BACKGROUND AND SUMMARY OF THE INVENTION

The present invention relates to an automatic electronic span circuit including means for automatically adjusting the gain of an amplifier to make its output correspond to a predetermined value. The invention is particularly useful in connection with programmed analytical instruments where standard samples of known compositions are periodically introduced into the instrument as calibration checks.

In many field applications of analytical instruments, it is important to automatically change the gain of the analyzer amplifier to make the output voltage or current agree with the known composition of a reference sample. This is usually accomplished by means of a servo system which drives a gain control, or attenuator, potentiometer to a point such that the output agrees with a preselected reference voltage. For example, a 68 ppm (parts per million) standard sample may be used where the full scale span of the analyzer is 100 ppm. A reference voltage of 68% of full scale may then be set so that when the standard sample is introduced into the analyzer the span servo is programmed on to set the gain control to a point where the output is precisely 68% of full scale. Then, when the servo is turned off, the gain setting remains until the next programmed span adjustment. The major disadvantages of the servo system are the initial cost and high maintenance level due primarily to the wear of the mechanical parts.

The present invention provides an automatic span circuit which electronically performs the same function upon the output of an analyzer as does the servo system, but with no moving parts. The gain of an analyzer amplifier is adjusted or controlled by a digital generated by the span circuit in such a manner that the output of the amplifier from a given standard sample is made to be equal to a given reference voltage. The digital circuit, when deactivated, maintains a status quo condition such that the gain set immediately prior to deactivation is retained until the next setting or "span" cycle. A direct current electrical signal voltage generated by a sample analyzer is fed to the analog input of a conventional multiplying digital-to-analog converter (MDAC), the analog output of which is connected to one input of an analog comparator and compared to a reference voltage connected to the other comparator input. The reference voltage, which may be obtained from the adjustable contact of a potentiometer connected across a battery, is set at a voltage less than the output of the analyzer for the standard sample, since the gain of the MDAC is less than 1. The comparator generates at its output one of two voltage levels depending on whether the MDAC output voltage is larger or smaller than the reference voltage. The comparator output is connected to two electronic gates which selectively transmit voltage pulses from a pulse generator to the UP or DOWN inputs of a binary UP/DOWN counter having its digital output counting channels connected, respectively to the digital input channels of the MDAC in such manner that the UP/DOWN counter counts UP when the MDAC output voltage is smaller than the reference voltage, and counts DOWN when the MDAC output voltage is larger than the reference voltage. These digital inputs to the MDAC automatically adjust the gain of the MDAC amplifier, up or down, until the MDAC output voltage is equal to the reference voltage. In a short time, the calibration of the MDAC to the particular reference voltage used is completed, and the electronic gates are disabled, manually or automatically. The MDAC remains connected to the UP/DOWN counter, and hence, retains the final digital input and gain adjustment. A visual and/or recording voltmeter, connected between the MDAC output and ground, is calibrated to read the known input voltage to the MDAC, or the known concentration in ppm of the standard sample, instead of the actual output voltage. The actual output voltage is the actual input voltage x the fixed fractional gain of the MDAC.

When the circuit described is then used to measure an unknown sample, the output voltage thereof, or concentration in ppm, is indicated directly by the calibrated meter.

At any time thereafter, the automatic span circuit can be recalibrated, by introducing the same or a different standard sample of known concentration adjust the gain of the MDAC, and re-calibrating the meter, as in the initial calibration.

BRIEF DISCRIPTION OF THE DRAWING

The single FIG. in the drawing is a circuit diagram of an automatic span circuit incorporating the invention.

DETAILED DESCRIPTION OF A PREFERRED EMBODIMENT

The drawing shows an automatic span circuit 1, comprising an N-channel (N >1) multiplying digital-to-anode converter (MDAC) 3 having its analog input 5 connected to the analog voltage output 7 of a chemical analyzer 9 having a power supply 11. For example, the analyzer 9 may be designed to measure the concentration of a particular element or compound in the composition of a standard sample and produce an analog voltage output proportional to the desired concentration in ppm. The MDAC, which is commercially available, has the characteristic that its analog output is a linear function of the product of its analog input and its digital input. For example, a 12-channel MDAC, with possible digital inputs from 0 to $2^{13}-1$ (or 4095), having a digital input of 3276 would have a fractional gain of 3276/4095, or 0.8, and an analog output equal to 0.8 × its analog input. The digital input channels 13 (e.g. 12 channels) are connected respectively to the same number of digital input channels 15 of a binary UP/DOWN digital counter 17 having UP and DOWN clock inputs 19 and 21, respectively. Alternatively, a counter having a single combined UP/DOWN input may be used. The analog output 23 of the MDAC 9 is connected to one input 25 of a voltage comparator 27. The other input 29 of comparator 27 is connected to the adjustable contact 31 of a potentiometer 33 energized by a dc voltage source or battery 35 having its negative terminal 37 connected to ground 39. The voltage of source 35 should be somewhat less than the full scale voltage of analyzer 9. The contact 31 is adjusted to produce a suitable reference voltage. If the known output voltage of the standard sample used in the analyzer is 60% of full-scale analyzer voltage, the contact 31 is set at about the same 60% of full-scale of the potentiometer 33. If the full-scale analyzer voltage is 10 volts and the full-scale voltage of the potentiometer is about 8 volts, then the MDAC input voltage will be 6 volts, the MDAC output voltage will be 6 × 0.8 = 4.8 volts, and the reference voltage at 31 will be about 0.6 × 8 = 4.8 volts.

In accordance with the invention, the gain of MDAC 9 is automatically adjusted by the counter 17, in response to the MDAC output and reference voltages, to make these voltages exactly equal. To accomplish this result, the output 41 of comparator 27 is connected directly to one input 43 of a first NOR gate 45 and, through an inverter 47, to one input 49 of a second NOR gate 57. The outputs 53 and 55 of NOR gates 45 and 51 are connected to the DOWN and UP inputs 21 and 19, respectively, of counter 17. The other inputs 57 and 59, respectively, of NOR gates 45 and 51 connected to the output 61 of an enabling NAND gate 63. One input 65 of NAND gate 63 is connected to the output 67 of a pulse generator 69. The other input 71 of NAND gate 63 is connected, either directly or through suitable programming means (not shown), to the analyzer for automatic control of gate 63.

A voltage-responsive, indicating and/or recording meter 73 is connected between the MDAC output 23 and ground 39.

The circuit 1 is operated as follows. Assume that the MDAC analog input is 6 volts and the reference voltage is about 4.8 volts, as in the example given above, but the digital input to the MDAC is some number other than 3276. NAND gate 63 is opened by applying a logical ONE to input 71, thereby permitting the transmission of pulses from generator 69 to the two NOR gates 45 and 51. If the amplified MDAC output voltage is less than the fixed reference voltage, the comparator 27 will produce a logical ONE, which blocks the transmission of pulses through NOR gate 45 but, through inverter 47, applies a logical ZERO to NOR gate 51, thereby opening NOR gate 51 to transmission of pulses to the UP input 19 of counter 17. Counter 17 then automatically counts UP, thereby increasing the digital input and gain of the MDAC, until the MDAC output voltage is equal to the reference voltage. If the MDAC output voltage is higher than the reference voltage, the comparator 27 will produce a ZERO output, which closes NOR gate 51 while opening NOR gate 51 to transmission of pulses to the DOWN input to counter 17, which decreases the digital input and gain of the MDAC until the two voltages are equal. In each case, NAND gate 63 inverts the pulse train from generator 69, and each of NOR gates 45 and 51 inverts the pulse train back. The digital input from the analyzer to NAND gate 63 may be automatic or manual, applied during the analysis of the sample and the automatic adjustment of the MDAC gain.

After a short period of operation, the MDAC output voltage will be equal to the reference voltage output (4.8 volts in the example given). Then, the meter 73 is calibrated, from 0 to the full-scale output of the analyzer (e.g. 10 volts) in volts and/or ppm, to register the output voltage and/or concentration of the standard sample, instead of the actual (fractionally-amplified) voltage at that point. Then, the MDAC digital input and gain are fixed, by closing NAND gate 63 to pulses, i.e. by changing the ONE to a ZERO on input 71, thereby inactivating both NOR gates 45 and 51, and the input to the counter 71. This completes the calibration of the span circuit for the particular standard sample and reference voltage used. The error in adjusting the gain of the MDAC will be less than 1/4096, or 0.0244%, for a 12 channel counter and MDAC.

The calibrated span circuit 1 can now be used to accurately measure the output voltage or concentration of an unknown sample merely by reading the meter 73.

At any subsequent time, the span circuit 1 can be re-calibrated in the same manner using the same or a different known standard sample, with the same or a different reference voltage.

Instead of a potentiometer and battery, any stable voltage source of suitable voltage can be used, but the potentiometer is preferred for flexibility. Also, other combinations of gates can be used.

Once the potentiometer has been set to produce a suitable reference voltage, and the meter 73 has been calibrated, the automatic span circuit 1 can be completely unattended.

What is claimed is:

1. An automatic gain control system comprising:
   a multiplying digital-to-analog converter having an analog voltage input, an analog voltage output, and N digital input channels, where N is an integer greater than one, and having the characteristic that its analog output is a linear function of the product of its analog input and its digital input;
   a binary UP/DOWN counter having N digital counting channels connected, respectively, to said N converter channels, and UP/DOWN counting input means;
   a fixed reference voltage source;
   a voltage comparator having two inputs, one connected to the analog voltage output of said converter and the other connected to said reference voltage source, and a binary output;
   means for generating a pulse train;
   gate means, controlled by said binary output of said comparator, for connecting said pulse train generating means to said input means to cause said counter to count UP when the analog output voltage from said converter is less than the reference voltage and to count DOWN when the analog output voltage is greater than the reference voltage; and
   a voltage-responsive meter, connected to said analog voltage output of said converter, calibrated to register the analog voltage input to said converter.

2. A system as in claim 1, wherein said input means comprises an UP counting input and a DOWN counting input; said comparator output is zero when said analog output voltage is greater than said reference voltage, and ONE when said analog output voltage is less than said reference voltage; and said gate means includes first and second electronic gates, each having two inputs and one output; one input of each gate connected to said pulse train generating means, the other input of the first gate connected directly to said comparator output and the other input of the second gate connected through an inverter to said comparator output, and the outputs of said first and second gates connected to said DOWN and UP counting inputs, respectively, of said counter.

3. A system as in claim 2, wherein said pulse train generating means and said gates are connected by an enabling third electronic gate.

4. A system as in claim 3, wherein said first, second and third gates are inverting gates, whereby the pulse train from said generating means is inverted by said third gate and then inverted back by each of said first and second gates.

5. A system as in claim 4, wherein said first and second gates are NOR gates, and said third gate is a NAND gate having two inputs and one output, one input connected to said pulse train generating means, the other being connected to said first and second gates; whereby: a ZERO comparator output opens said first gate to pulses and closes said second gate, causing said counter to count DOWN; a ONE comparator output closes said first gate to pulses and opens said second gate, causing said counter to count UP; a ONE input to said third gate opens that gate to pulses and starts said counter; and a ZERO input to said third gate closes that gate to pulses, stops said counter, and effectively isolates said gates from said counter and comparator.

6. A system as in claim 1, wherein said analog voltage input of said converter is connected to a source of known voltage;

said reference voltage source provides a fixed reference voltage that is lower than said known voltage; and the gain of said converter is automatically varied by said counter in response to said comparator output to make the analog output voltage of said converter substantially equal to said reference voltage.

7. A system as in claim 6, wherein said reference voltage source comprises a fixed but normally-movable contact of a potentiometer.

8. A system as in claim 1, adapted to be used with said gate means closed, and without changing the gain of said converter, to measure the voltage of an unknown analog input voltage source, as registered by the output of said meter.

9. An automatic span circuit comprising the combination of:

the automatic gain control system of claim 1; and an analyzer for measuring the concentration of a particular element or compound in the composition of a sample and producing an analog voltage output proportional to the measured concentration, with said analog voltage output connected to said analog voltage input of said converter.

* * * * *